United States Patent
Lochmann

(10) Patent No.: US 9,682,410 B2
(45) Date of Patent: Jun. 20, 2017

(54) BAR MADE OF NOBLE METAL, AND PRODUCTION METHOD

(75) Inventor: Dominik Lochmann, Rheinstetten (DE)

(73) Assignee: ESG EDELMETALL-SERVICE GMBH & CO KG, Rheinstetten (DE)

(*) Notice: Subject to any disclaimer, the term of this patent is extended or adjusted under 35 U.S.C. 154(b) by 432 days.

(21) Appl. No.: 13/391,227

(22) PCT Filed: Jun. 15, 2011

(86) PCT No.: PCT/EP2011/059879
§ 371 (c)(1),
(2), (4) Date: Mar. 7, 2013

(87) PCT Pub. No.: WO2011/107616
PCT Pub. Date: Sep. 9, 2011

(65) Prior Publication Data
US 2013/0189535 A1    Jul. 25, 2013

(30) Foreign Application Priority Data

Jun. 15, 2010 (DE) .......... 10 2010 030 128
Nov. 20, 2010 (DE) .......... 10 2010 044 199

(51) Int. Cl.
*B21C 37/04* (2006.01)
*A61K 6/04* (2006.01)
(Continued)

(52) U.S. Cl.
CPC ............ *B21C 37/045* (2013.01); *A61K 6/046* (2013.01); *B21C 37/02* (2013.01); *B21H 8/00* (2013.01);
(Continued)

(58) Field of Classification Search
CPC ....... Y10T 29/49826; Y10T 428/12201; B21C 37/02
(Continued)

(56) References Cited

U.S. PATENT DOCUMENTS 5,799,386 A    9/1998  Ingersoll et al.
2010/0233412 A1  9/2010  Wong et al.

FOREIGN PATENT DOCUMENTS

CA    2279426 A1   6/1999
DE    2107213 A    8/1972
(Continued)

OTHER PUBLICATIONS

Northwest Territorial Mint, "Stagecoach Silver Bars", Aug. 28, 2009, http://bullion.nwtmint.com/silver_stagecoach.php, accessed via Wayback Machine on Mar. 6, 2015.*
(Continued)

*Primary Examiner* — Humera Sheikh
*Assistant Examiner* — Lucas Wang
(74) *Attorney, Agent, or Firm* — Mannava & Kang, P.C.

(57) ABSTRACT

A bar of noble metal or an alloy containing noble metal having a mass mB is subdivided into n×m miniature bars 2, 3 each having a specified mass mk, wherein n and m each denote an integer ≥2, there being an interconnection of solid material (8) between directly adjacent miniature bars (2, 3). Another bar is affixed to a backing (13), to which the miniature bars are releasably attached. A method for the production of the bar consists in dividing up the same while leaving an interconnection of solid material or producing an arrangement thereof on a backing.

20 Claims, 3 Drawing Sheets

(51) Int. Cl.
*B21C 37/02* (2006.01)
*B21K 23/00* (2006.01)
*B21H 8/00* (2006.01)

(52) U.S. Cl.
CPC ......... *B21K 23/00* (2013.01); *Y10T 29/49826* (2015.01); *Y10T 428/12201* (2015.01)

(58) Field of Classification Search
USPC ........................................................ 40/27.5
See application file for complete search history.

(56) References Cited

FOREIGN PATENT DOCUMENTS

| DE | 3040052 A1 | 6/1982 | | |
|---|---|---|---|---|
| DE | 69415531 T2 | 7/1999 | | |
| DE | 102004060730 A1 | 6/2006 | | |
| EP | 0709473 B1 | 5/1996 | | |
| FR | 348205 A | 4/1905 | | |
| FR | 1152976 A | 2/1958 | | |
| GB | 939303 A | 10/1963 | | |
| JP | S57-22829 | 2/1982 | | |
| JP | 1133395 A | 5/1989 | | |
| JP | 3019393 A | 1/1991 | | |
| JP | H03-019393 | 1/1991 | | |
| JP | 2006-514335 | 4/2006 | | |
| WO | 9929281 A2 | 6/1999 | | |
| WO | 0016932 A1 | 3/2000 | | |
| WO | WO2009040109 | * | 4/2009 | ............... B28D 5/00 |

OTHER PUBLICATIONS

Gold Bars Worldwide, "How minted gold bars are manufactured", Nov. 2008, http://www.goldbarsworldwide.com/PDF/RT_2_HowMinted.pdf, accessed via Wayback Machine on Mar. 9, 2015.*
The Chocolate Store, "Candy Buttons", Jan. 6, 2011, http://www.thechocolatestore.com/pd-89-4-candy-buttons-4-6.aspx, accessed via Wayback Machin on Mar. 9, 2015.*
Machine Translation of WO/2009/040109, EPO, accessed Mar. 19, 2015.*
Party City, "Necco Candy Buttons", http://www.partycity.com/product/necco+candy+buttons+1.5oz.do, accessed Sep. 1, 2015.*
Alibaba, "Stagecoach Divisble Bars", http://guide.alibaba.com/shop/stagecoach-divisable-bar-encased-in-air-tite-direct-fit-capsule-1-troy-ounce-999-pure-silver-art-bar-accepted-worldwide-currency-collectable-precious-metal_4752298.html, accessed Sep. 1, 2015.*
International Search Report for and Written Opinion for PCT Application PCT/EP2011/059879, European Intellectual Property Office, Nov. 18, 2011.
European Office Action for 11 731 292.6, Jul. 5, 2012.
English translation of the International Preliminary Report on Patentability for International Application PCT/EP2011/059879, The International Bureau of WIPI, Dec. 19, 2012.
European Office Action for Application No. 11 731 292.6, dated Jul. 5, 2012.
"Challenge Coins, Commemorative Medallions and Bullion from Northw . . . " Download date: Feb. 13, 2013.

* cited by examiner

BAR MADE OF NOBLE METAL, AND PRODUCTION METHOD

PRIORITY

The present application claims priority under 35 U.S.C. §371 to PCT Application PCT/EP2011/059879, filed on Jun. 15, 2011, which claims priority to German Patent Application No. 10 2010 044 199.6, filed on Nov. 20, 2010, and German Patent Application No. 10 2010 030 128.0, filed on Jun. 15, 2010, the disclosures of which are hereby incorporated by reference in their entireties.

The invention relates to a bar of noble metal, for example, gold, silver, platinum, palladium or alloys thereof and to a method for the production of such a bar.

PRIOR ART

Proportionable dental gold materials are commercially available in the form of platelets, the platelets having been obtained by producing identical pieces from rolled sheet gold. The sheet gold is made by rolling an alloyed gold bar, as described in DE 10 2004 060 730 A1.

For the production of gold bars in small pieces, i.e. pieces weighing 1 g, 5 g, or 10 g it is known to stamp information concerning the weight, the manufacturer, the purity of the metal, and the type of metal onto each single bar. Bars of noble metal in small pieces are very popularly with investors but are individually expensive to produce in relation to the metal price.

SUMMARY OF THE INVENTION

Instead of making a large number of individual miniature bars each of a specified mass mk, the fundamental idea of the invention consists in producing, in a single pass, a plaque or bar having a mass mB and comprising a plurality of such miniature bars and subsequently dividing up this plaque or bar by complete or partial separation of material to form the miniature bars, whilst the miniature bars are disposed in an n×m arrangement in which each of n, m≥2. Thus the total mass mB of the bar is given by n×m×mk.

Due to the fact that there is first produced a bar in the form of a plaque of a nominal mass mB, which is then divided up into a plurality of miniature bars, for example by embossing, which miniature bars may, if required, be separated from each other or lifted from a backing without the use of tools, there is both a reduction in the manufacturing costs and an improvement in the handling of the miniature bars.

Thus the invention relates to a bar of noble metal or an alloy containing a noble metal having a mass mB, which bar is subdivided into n×m miniature bars each of a specified mass mk, wherein n and m each denote an integer ≥2. Between the directly adjacent miniature bars there is an interconnection of solid material such that the miniature bars are firmly attached to their direct neighbors. The interconnecting material can, for example, be in the form of a bridge or a connecting land.

Advantageously, the interconnection of solid material can have a predetermined break point. The bending strength of the interconnection is preferably such that bending by the force of gravity is not possible, whereas its upper limit is such that destruction of the interconnection of solid material is possible by manually bending or breaking the same.

In addition to the interconnection of solid material, or alternatively thereto, the underside of the bar may be provided with a backing material such that when the miniature bars are produced from a bar or from a plaque, they can be completely separated without the provision of an interconnection of solid material with or without a predetermined break point.

The interconnection of solid material can advantageously form part of a depression provided in the bar. A depression may be formed on the top surface and an opposing depression on the underside, and the interconnection of solid material can be set at a distance from the top surface and from the underside of the bar. The depression can be in the form of a groove.

Another object of the invention is a bar of noble metal or an alloy containing a noble metal and having a mass mB, which bar is subdivided into n×m miniature bars each having a specified mass mk, wherein n and m each denote an integer ≥2 whilst a backing material is attached to the underside of the bar and the miniature bars are peripherally spaced all round from their adjacent miniature bars and are exclusively attached to said backing.

Advantageously, the miniature bars can be separated from each other via a depression that penetrates the bar down to the backing.

It is particularly advantageous when the depression is impressed, since by this means economical production is possible.

Another object of the invention is a method for the production of a bar having a mass mB consisting of noble metal or an alloy containing noble metal, in which the bar is in one manufacturing step divided up into n×m miniature bars, each of a specified mass mk, wherein n and m each denote an integer ≥2, whilst in between the directly adjacent miniature bars there remains an interconnection of solid material.

The interconnection of solid material can advantageously form part of a depression.

Yet another object of the invention is the provision of a method for the production of a bar having a mass mB consisting of noble metal or an alloy containing noble metal, in which the bar is affixed, in one manufacturing step, to a backing material and, in another manufacturing step, is divided up into n×m miniature bars each of a specified mass mk, wherein n and m each denote an integer ≥2, and the miniature bars are peripherally spaced all round from the adjacent miniature bars and are attached exclusively to the backing material.

Advantageously, the bar can be embossed to effect said division into miniature bars.

Yet another object of the invention is the provision of a method for the production of a bar having a mass mB consisting of noble metal or an alloy containing noble metal, in which a continuous band of noble metal of appropriate thickness is rolled and fed stepwise to a shaping device and is advanced following shaping. The shaping consists in dividing up the continuous band into a row comprising n×1 miniature bars each having a specified mass mk, wherein n denotes an integer ≥2, while leaving an interconnection of solid material between directly adjacent miniature bars and the continuous band. This makes it possible to form a continuous composite bar.

The desired bar is produced by severing the interconnection of solid material in the region between a row and the rest of the continuous band following on a specified number of rows.

The continuous band can have a width B which is greater than the width b of the bar to be fabricated, so that when the continuous band is shaped, it is augmented by a protruding edge.

If shaping includes automatic removal of said edge, it will be possible to carry out such severing of the continuous band following the production of a desired number of rows, to produce the finished bar.

Advantageously, the miniature bars formed during shaping can be simultaneously inscribed.

BRIEF DESCRIPTION OF THE DRAWINGS

Exemplary embodiments of the invention are illustrated in the drawings, in which.

DESCRIPTION OF EXEMPLARY
EMBODIMENTS OF THE INVENTION

Figure 1:
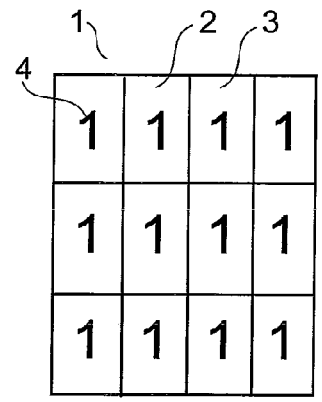
FIG. 1 illustrates a bar of noble metal in the form of a plaque containing 4×3 miniature bars.

FIG. 1 illustrates a bar 1 of noble metal in the form of a plaque comprising 4×3 miniature bars 2, 3. To this end, a bar (not shown) was first of all produced in the form of a plaque having a nominal mass mB. Processing of the bar to provide a plurality of miniature bars 2, 3 can be effected, for example, by embossing. This can take place at the same time as an embossing operation by means of which the data 4 concerning the miniature bars 2, 3 are impressed, namely a manufacturer's logo, the mass and the purity, such that production can take place in a single pass. In the exemplary embodiment shown, the parameter 4 indicating the mass is shown as "1", which denotes 1 g.

Figure 2:
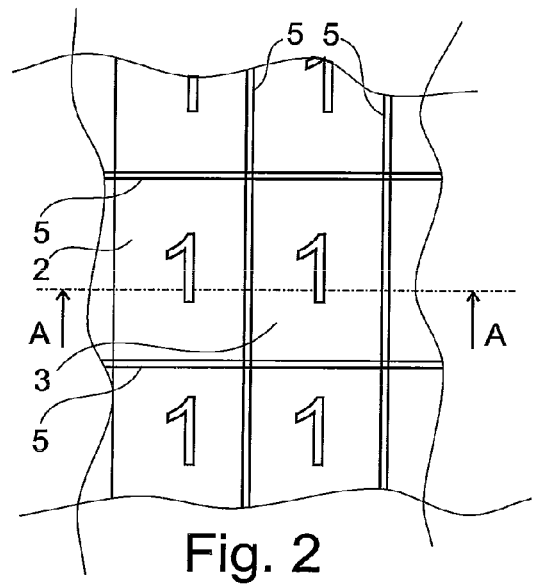
FIG. 2 shows a detail of FIG. 1.

As shown in FIG. 2 in detail, the shaping operation has involved the creation of depressions in the bar 1 at specific intervals, such depressions being in the form of grooves 5, which distinctly delimit the individual miniature bars 2 with respect to the adjacent miniature bars 3. The position of the grooves 5 in the bar 1 is selected such that the miniature bars 2, 3 delimited by the grooves 5 have the desired mass.

Preferably, the bar can have a specified uniform thickness prior to the shaping operation, so that shaping of the bar can be carried out by means of a single embossing punch, while the mass of the miniature bars 2, 3 will be sufficiently correct, that is, within permissible tolerances.

An example of how a bar can be produced in the form of a plaque is illustrated by a fine gold bar having a mass of 100 g being subdivided into 100 miniature bars each weighing 1 g. For this purpose, a continuous metal band of 99.99% fine gold is previously rolled to a calculated thickness. Plaques weighing 100 g are punched out of this band.

These plaques are embossed in an embossing machine known per se for embossing coins, in a similar manner thereto and in a single pass such that depressions in the form of grooves 5 are formed between the individual miniature bars, and that the manufacturer's logo, the weight and the purity are inscribed on each individual 1 g miniature bar.

The depressions 5, 5' in the form of grooves can be so thin that the displaced material forms only a comparatively small lateral bead, which can, however, be flattened immediately on the surfaces, if desired, by the embossing operation. In this context, "thin" means that the width of the depression is smaller than its depth and is preferably not more than 50% of its depth.

Figure 3:
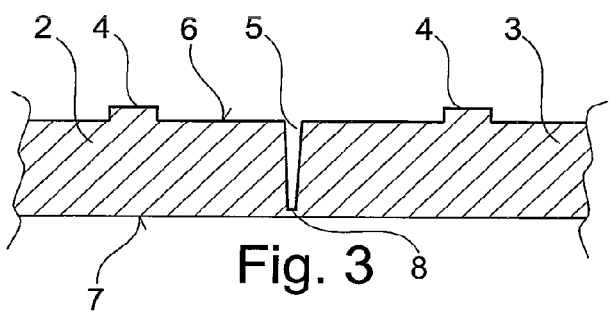
FIG. 3 is a partial section taken along the line A-A of FIG. 2.

FIG. 3 is a partial cross-section taken along the line A-A of FIG. 2, and it can be seen that the depressions 5 do not penetrate the entire plaque but that a groove 5 is formed that extends from the top surface 6 toward the underside 7, the interconnection of solid material 8 being in the form of a connecting land (see the description of FIGS. 4A-4D below), or of a bridge (see the description of FIGS. 5A-5D below).

The interconnection of solid material 8 in the depression 5 can take various shapes, as shown in FIGS. 4A-4D and 5A-5D, for example.

Figure 4A:
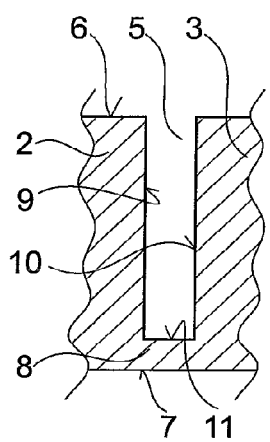
FIGS. 4A-4D show various forms of an interconnection of solid material between the miniature bars in a plaque.

In FIG. 4A, the side walls 9, 10 of the depression 5 formed only from the top surface of the plaque are substantially parallel to each other and perpendicular to the top surface 6 and the underside 7 of the plaque, the base 11 of the depression 5 being flat and parallel to the underside 7. The base 11 is part of the connecting land of the interconnection of solid material 8 between adjacent miniature bars 2, 3.

Figure 4B:
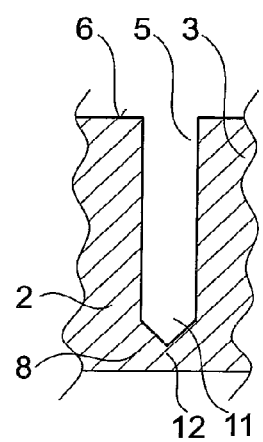

FIG. 4B differs from FIG. 4A in that the base 11 of the depression is tapered toward the underside such that a predetermined break point 12 is formed at the point of greatest depth of the base 11 on account of the smallest cross-section of the connecting land at said point.

With the presence of a predetermined break point 12, the interconnection of solid material 8 in the depression 5 can, if required, be broken without the use of a tool to allow the miniature bars to be separated from each other. By reason of the known position of the predetermined break point, a planned weight distribution is ensured.

Figure 4C:
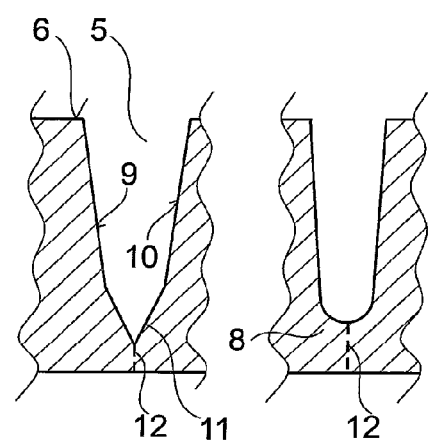

In FIG. 4C, the side walls of the depression 5, which is created only from the top surface 6 of the plaque, are tapered toward the base, the base 11 of the depression 5 being steeply tapered as in FIG. 4B. This produces a predetermined break point 12. In cross-section, the depression shows two different angles of spread, the angle of spread of the base 11 being larger than that of the side walls 9, 10.

Figure 4D:
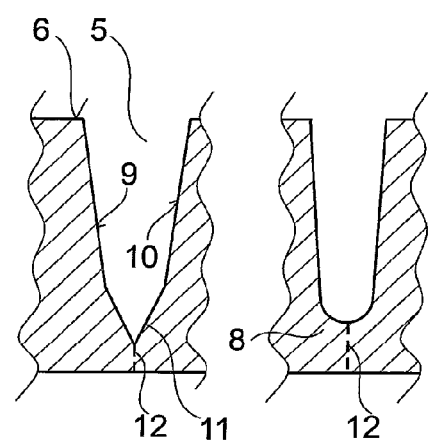

In FIG. 4D, the side walls are as in FIG. 4C, whereas the base 11 is rounded, somewhat like a gutter. Here again, the predetermined break point 12 is in the region of the smallest cross-section of the connecting land 8.

FIGS. 5A-5D illustrate other forms of an interconnection of solid material 8 having, in some cases, a predetermined break point 12 between the miniature bars 2, 3 in a plaque, differing from FIGS. 4A-4D in that the interconnection of solid material is disposed in a depression 5,5' that is created both from the top surface 6 and from the underside 7. In this case, the material is displaced both at the top surface 6 and at the underside 7 and can, if desired, be flattened during the embossing operation.

Figure 6:
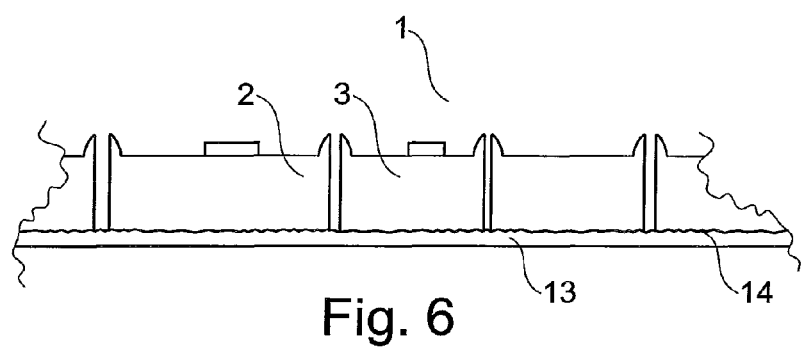
FIG. 6 shows miniature bars disposed on a backing and not interconnected by solid material.
Figures 5A, 5B, 5C, 5D:
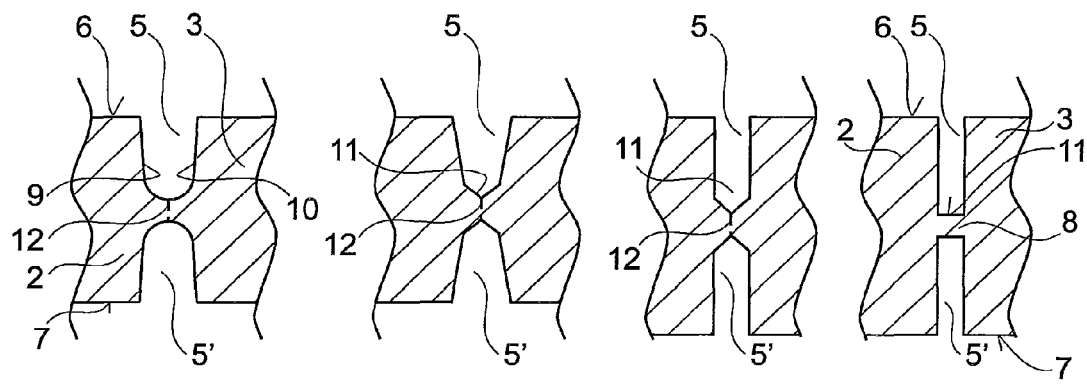
FIGS. 5A-5D show other forms of an interconnection of solid material between the miniature bars in a plaque.

In FIG. 6, the plaque 1 is disposed with its underside 7 resting on a backing 13, to which it is attached by, say, adhesive means such that even when the miniature bars are completely separated, that is to say, are not interconnected by solid material, a certain degree of coherence is still given. The material can be intercepted by creating a depression 5 in the form of a groove, said depression being impressed from the top surface 6, that is, from the surface of the plaque opposite the backing 13.

A suitable backing 13 is, for example, a backing board provided with a gum coating 14 which is similar to that coated on self-adhesive labels and from which the individual miniature bars 2, 3 can be readily removed without any traces of adhesive remaining on the miniature bars 2, 3. The backing board can consist either of comparatively thick paper, of paperboard, or of plastics material.

Thus one or more of the miniature bars 2, 3 can be removed from the backing, while the remaining miniature bars stay on the backing 13 and can again be handled collectively.

Figure 7:
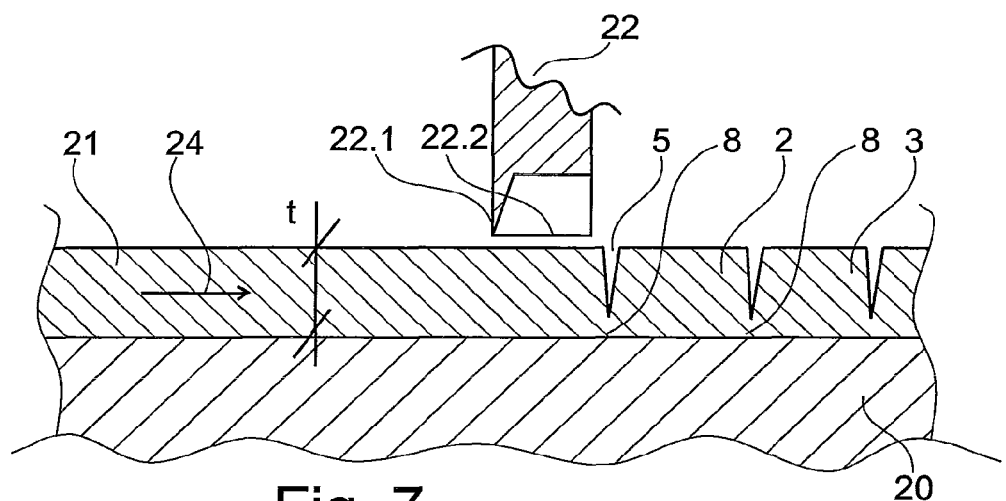
FIG. 7 is a cross-section of the continuous band comprising miniature bars.
Figure 8:
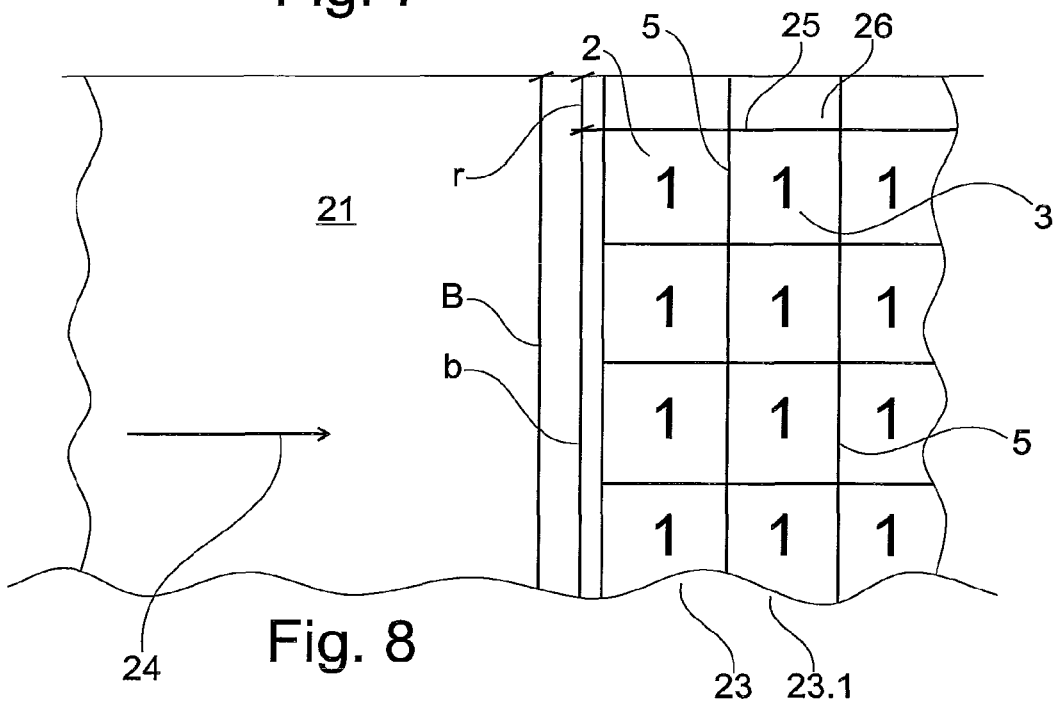
FIG. 8 is a top view of the shaped continuous band shown in FIG. 7.
Figure 9:
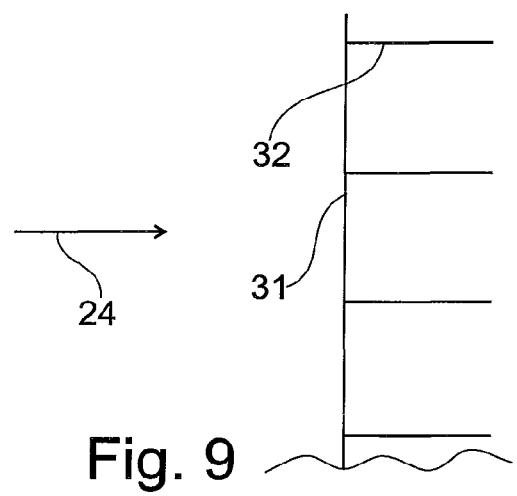
FIG. 9 shows edges of a tool for the production of miniature bars.

In another embodiment, illustrated in FIGS. 7 to 9, the bar 1 is produced by starting from a continuous band 21 as illustrated in cross-section in FIG. 7 and rolled to a precalculated thickness t and having a fine gold content of 99.99%, and shaping the continuous band 21 stepwise to form the miniature bars. To this end, the continuous metal band 21 resting on a table 20 is caused to approach a shaping station 22, and in a shaping step there are produced miniature bars 2 which comprise an interconnection of solid material 8 with a miniature bar 3 produced in the previous shaping step and in addition with the unshaped continuous band 21, in each case at the base of a depression 5 that takes the form of a groove. The depression 5 in the form of a groove is produced with a sharp edge 22.1, and another sharp edge 22.2 is shown in the direction of advance 24 for other grooves (not shown).

As may be seen from the top view shown in FIG. 8, the miniature bars 2, 3 are each disposed in a row 23, 23.1 at right angles to the direction of advance 24 of the continuous band 21 and are separated from each other by the groove-shaped depression 5.

On completion of shaping a row 23, the continuous metal band 21 is forwarded in relation to the shaping device (not shown) by one step and the shaping operation is repeated in order to produce the next row of miniature bars 2, 3. The bar itself can then be severed at a suitable point so as to give a bar having the desired number of rows 23 of miniature bars 2, 3.

When the continuous metal band 21 has a width B greater than the width b of the bar to be fabricated, each miniature bar 2, 3 is subjected to the same shaping operation during fabrication thereof. However, the lateral excess of material on the continuous metal band 21 beyond the width of the bar 1 produces a lateral edge 26 of width r separated by a depression 25 in the form of a groove extending in the direction of advance 25 but is still connected by solid material. The edge 26 can be removed during shaping or it can be removed after shaping.

This method of shaping can include the production of depressions 5 impressed both from the top surface of the continuous band 21 and from its underside. The additional provision of a groove produced from the underside is basically advantageously when the thickness of the bar is too great for shaping from one side only to be sufficient.

The predetermined break points produced by the formation of depressions 5 in the bar in the region of the interconnection of solid material 8 can have an angle of spread of from approximately 10 degrees to 60 degrees and the interconnection of solid material 8 can have a thickness of from 0.05 mm to 0.4 mm, although other thicknesses may be adequate for effecting manual separation.

FIG. 9 illustrates edges 31, 32 of a tool for the production of miniature bars. One edge 31 extends at right angles to the direction of feed 24 and produces the depression 5 in the form of a groove, another edge 32 in the direction of feed 24 produces, for example, the depression 25 in the form of a groove situated in the marginal region 26 of a miniature bar 2, 3 shown in FIG. 8. The edges 31, 32 are pressed into the continuous band and displace the material such that a depression is formed, whilst at the same time an interconnection of solid material remains, which is in this case not shown.

The embodiment illustrated in FIGS. 7 to 9 also includes the possibility of using backing material instead of an interconnection of solid material, said backing material being attached to the continuous band.

The bars are fabricated, for example, in the following sizes:

For gold 100×1 g: 74 mm×105 mm×0.667 mm or 85 mm×150 mm×0.406 mm; for silver: 100×1 g: 74 mm×105 mm×1.226 mm; for platinum: 100×1 g: 74 mm×105 mm×0.602 mm, and for palladium: 100×1 g: 74 mm×105 mm×1.073 mm.

Thus it is possible to differentiate between two fabrication variants, although other manufacturing processes, such as casting, are not unfeasible. In the first variant, a noble metal sheet is cut to the final dimensions of the finished product. The cut sheet then passes to a normal embossing machine, such as is used for embossing coins or standard noble metal bars, where it is embossed to produce the final shape using appropriately shaped embossing punches under high pressure.

In the second variant, a continuous band of noble metal of a desired thickness is rolled and forwarded to a punching machine, in which a complete row, for example comprising 10 miniature bars weighing 1 g each, is simultaneously notched and inscribed. The band is then advanced such that a continuous composite is produced, which is severed after every tenth row to give a composite bar containing pieces weighing 10×10×1 g.

Both variants are suitable for achieving high-gloss surfaces.

The invention claimed is:

1. A bar of noble metal or an alloy containing noble metal having a mass mB, the bar being subdivided into a total of n×m miniature bars, each miniature bar having a specified mass mk, wherein n and m each denote an integer ≥2 and directly adjacent miniature bars include an interconnection of solid material therebetween,
wherein the interconnection of the solid material includes a thickness adequate for separation of the miniature bars from each other at a predetermined break point that is located at a greatest depth of a depression formed in the bar, and
wherein the interconnection of the solid material includes the thickness adequate for separation of the miniature bars from each other at the predetermined break point without the use of tools.

2. The bar according to claim 1, wherein a backing is attached to an underside of the bar.

3. The bar according to claim 1, wherein there is a depression on a top surface of the bar and a depression opposite thereto on an underside of the bar, and that the interconnection of the solid material is set at a distance from the top surface of the bar and from the underside of the bar.

4. A bar of noble metal or an alloy containing noble metal having a mass mB and a backing adhesively attached to an underside of the bar, the bar being subdivided into a total of n×m miniature bars, each miniature bar having a specified mass mk, where n and m each denote an integer ≥2 and the miniature bars are peripherally spaced from adjacent miniature bars and are adhesively attached exclusively to the backing upon breaking of an interconnection of solid material between the miniature bars, wherein the backing is made of a material that is different from the noble metal or the alloy containing noble metal in the bar.

5. The bar according to claim 4, wherein the miniature bars are separated from each other by a depression penetrating the bar down to the backing.

6. The bar as defined in claim 5, wherein the depression is impressed.

7. A method for production of a bar including noble metal or an alloy containing noble metal having a mass mB, the method comprising:
   dividing the bar into a total of n×m miniature bars, each miniature bar having a specified mass mk, wherein n and m each denote an integer ≥2; and
   interconnecting directly adjacent miniature bars by solid material, wherein the solid material between each miniature bar has a cross-section having a first thickness at each edge adjacent to each of the miniature bars and a second thickness at a center of the solid material, wherein the first thickness is greater than the second thickness, and wherein the second thickness is adequate for separation of the miniature bars from each other at a predetermined break point without the use of tools.

8. A method for production of a bar including noble metal or an alloy containing noble metal having a mass mB, the method comprising:
   adhesively attaching the bar to a backing;
   dividing the bar into a total of n×m miniature bars, wherein each miniature bar remains adhesively attached to the backing upon breaking of an interconnection of solid material between the miniature bars, wherein each miniature bar includes a specified mass mk, and wherein n and m each denote an integer ≥2; and
   peripherally spacing the miniature bars from the adjacent miniature bars.

9. A method for production of a bar having a mass mB of noble metal or an alloy containing noble metal in which a continuous band of noble metal is rolled to a desired thickness and is fed stepwise to a shaping device and moved away therefrom following shaping, the method comprising:
   during the shaping, dividing the continuous band into a row of a total of n×1 miniature bars, each miniature bar having a specified mass mk, where n denotes an integer ≥2; and
   leaving an interconnection of solid material between directly adjacent miniature bars and the continuous band,
   wherein the interconnection of the solid material has a predetermined break point that is located at a greatest depth of a depression formed in the bar, and
   wherein the interconnection of the solid material has the predetermined break point for separation of the miniature bars from each other without the use of tools.

10. The method according to claim 9, further comprising severing the shaped continuous band in the region of the interconnection of the solid material between a row and the continuous band following creation of a specified number of rows, for the production of the bar.

11. The method according to claim 9, wherein the continuous band has a width B which is greater than a width b of the bar to be fabricated such that shaping produces, in addition to the bar, a protruding edge.

12. The method according to claim 9, wherein the miniature bars are inscribed during production thereof.

13. The bar according to claim 1, wherein the depression includes a tapered end section that includes a width which is less than approximately 50% of a depth of the tapered end section.

14. The bar according to claim 1, wherein the depression includes side walls that are parallel, and a bottom surface that is generally perpendicular to the side walls.

15. The bar according to claim 1, wherein the depression includes side walls that are parallel, and a bottom surface that is generally transverse to the side walls.

16. The bar according to claim 1, wherein the depression includes side walls, and each of the side walls is tapered to include two differently angled slopes.

17. The bar according to claim 1, wherein the depression includes side walls that are tapered, and a bottom surface that includes a generally U-shaped cross section.

18. The bar according to claim 1, wherein each of the miniature bars includes a mass mk, a manufacturer's logo, and a purity impressed thereon.

19. The bar according to claim 1, wherein the depression includes a tapered end section.

20. The bar according to claim 1, wherein the predetermined break point is located in a region of a smallest cross section of the interconnection of the solid material.

* * * * *